US008624018B2

(12) United States Patent
Iguchi

(10) Patent No.: US 8,624,018 B2
(45) Date of Patent: Jan. 7, 2014

(54) PROBE, POLYMORPHISM DETECTION METHOD, METHOD OF EVALUATING DRUG EFFICACY OR TOLERANCE, AND REAGENT KIT

(75) Inventor: Aki Iguchi, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 0 days.

(21) Appl. No.: 13/458,715

(22) Filed: Apr. 27, 2012

(65) Prior Publication Data

US 2012/0282608 A1 Nov. 8, 2012

(30) Foreign Application Priority Data

May 2, 2011 (JP) ................................. 2011-102986
Mar. 30, 2012 (JP) ................................. 2012-082392

(51) Int. Cl.
*C07H 21/04* (2006.01)
(52) U.S. Cl.
USPC ...................................... 536/24.31; 435/6.11
(58) Field of Classification Search
None
See application file for complete search history.

(56) References Cited

U.S. PATENT DOCUMENTS

2008/0311579 A1 12/2008 French et al.
2009/0131268 A1 5/2009 Hardenbol et al.

FOREIGN PATENT DOCUMENTS

| JP | 2002-119291 A | 4/2002 |
| JP | 4454366 B | 4/2010 |
| WO | 02/052044 A2 | 7/2002 |

OTHER PUBLICATIONS

Sun et al., Cancer Cemotherapy Pharmacology, published online Jul. 1, 2009, vol. 65, 437-446.*
Housni et al., Clinical Chemistry, 2003, vol. 49, pp. 1669-1672.*
Buck et al., Biotechniques, 1999, vol. 27, pp. 528-536.*
Behrens et al., System. Appl. Microbiol., 2004, vol. 27, pp. 565-572.*
Saito et al., Clinical Biochemsitry, 2003, vol. 36, pp. 511-518.*
Roy et al., Drug Metabolism and Disposition, 2005, vol. 33, pp. 884-887.*
Extended Search Report issued in corresponding European Patent Application No. 12166069.0 dated Aug. 22, 2012.
Applied Biosystems, "TaqMan Drug Metabolism Genotyping Assays-Reference Guide," (2010).
Unknown, "rs717620-TaqMan Drug Metabolism Genotyping Assays," (2010).
Drug response related SNP sequence, SEQ ID 1972, EBI Accession No. GSN: AWW31195 (2009).
Drug response related SNP sequence, SEQ ID 2436, Geneseq Database, EBI Accession No. GSN: AWW 31659 (2009).
Human ABCC2 gene SNP containing probe homology sequence, SEQ ID 787, Geneseq Database, EBI Accession No. GSN: AWW30010 (2009).
Ohmann et al., "Impact of Inosine 5'-Monophosphate Dehydrogenase 1,2 and Multidrug Resistance Protein 2 Genetic Polymorphisms on Mycophenolate Mofetil Related Adverse Events in Pediatric Heart Transplant Patients," The Journal of Heart and Lung Transplantation, 27: S181 (2008).
Crockett et al., "Fluorescein-Labeled Oligonucleotides for Real-Time PCR: Using the Inherent Quenching of Deoxyguanosine Nucleotides," Analytical Biochemistry, 290: 89-97 (2001).
Ozawa, et al. "Polymorphisms in the ABCC2 (CMOAT/MRP2) Gene Found in 72 Established Cell Lines Derived From Japanese Individuals: An Association Between Single Nucleotide Polymorphisms in the 5'-Untranslated Region and Exon 282" Drug Metabolism and Disposition, 30; 363-364 (2002).
Taheri et al. "Effect of MDR1 polymorphism on multidrug resistance expression in breast cancer patients." Genetics and Molecular Research, 9: 34-40 (2010).

* cited by examiner

*Primary Examiner* — Anne Gussow
*Assistant Examiner* — Mindy G Brown
(74) *Attorney, Agent, or Firm* — Morgan, Lewis & Bockius LLP

(57) ABSTRACT

A probe for detecting polymorphism in the ABCC2 gene is constituted by including, for example, an oligonucleotide which is complementary to a base sequence including the 207th to the 217th bases of the base sequence indicated in SEQ ID NO:1 and having a length of from 11 bases to 60 bases, and has an identity of at least 80%, and in which a base corresponding to the 217th base has been labeled with a fluorescent dye.

10 Claims, 4 Drawing Sheets

PROBE, POLYMORPHISM DETECTION METHOD, METHOD OF EVALUATING DRUG EFFICACY OR TOLERANCE, AND REAGENT KIT

This application claims priority from Japanese Patent Application No. 2011-102986 filed on May 2, 2011 and Japanese Patent Application No. 2012-082392 filed on Mar. 30, 2012, which are incorporated by reference herein in their entirety. All publications, patent applications, and technical standards mentioned in this specification are herein incorporated by reference to the same extent as if each individual publication, patent application, or technical standard was specifically and individually indicated to be incorporated by reference.

Sequence Listing Submission via EFS-Web: A computer readable text file, entitled "SequenceListing.txt," created on or about Jul. 10, 2012 with a file size of about 7 kb contains the sequence listing for this application and is hereby incorporated by reference in its entirety.

TECHNICAL FIELD

The present invention relates to a probe for detecting a polymorphism, a method of detecting a polymorphism, a method of evaluating the efficacy of a drug, and a reagent kit for detecting a polymorphism.

RELATED ART

The ABCC2 gene is localized in bile ducts of hepatocytes, and codes for a transporter that transports glutathione, glucuronic acid, and sulfate conjugates from a bile duct to a bile duct, and is considered to be involved in metabolism of various drugs.

In recent years, single nucleotide polymorphisms (SNPs) of the ABCC2 gene in Japanese people have been analyzed, and thus various gene polymorphisms have been discovered. It has also been suggested that there is a possibility that drug tolerance may be estimated by measuring C-24T, in which a cytosine (C) whose position is at 24 bases before the 5' end of the ABCC2 gene has been mutated into a thymine (T) (see, for example, Drug Metabolism and Disposition, 2002, Vol. 30, No. 4, pp. 363-364). Accordingly, a method, in which the polymorphisms in the ABCC2 gene may be measured correctly, in a short time, at a low cost and easily, is demanded.

In addition to the C-24T mutation, a large number of mutations, such as a C3435T mutation, in which a cytosine (C) that is the 3435th base in the exon 26 of the MDR1 gene has been mutated into a thymine (T), are known as mutations involved in drug sensitivity (see, for example, Japanese Patent Publication No. 4454366). Accordingly, it is thought that there is a possibility that drug tolerance may be estimated with a higher sensitivity by detecting not only a polymorphism(s) in the ABCC2 gene but also other mutant(s) involved in drug sensitivity together with the C-24T mutation.

At present, as a method of measuring a polymorphism of a gene, a PCR-RFLP method is known. In this method, PCR is carried out using a primer that has been designed so as to amplify a region containing bases that is desired to be measured; the products obtained by the amplification are subjected to cleaving with a restriction enzyme, that is selected so that the presence or absence of the cleaving by the restriction enzyme depends on whether the mutation of the particular base exists or not; and then, the resultant is electrophoresed to detect whether the products obtained by the amplification have been cleaved or not (see, for example, Genet. Mol. Res., 2010, 9(1), pp. 34-40).

In addition, a method in which a region containing a mutation is amplified by a PCR method; then, melting curve analysis is carried out using a nucleic acid probe that has been labeled with a fluorescent dye; and, based on the results of the melting curve analysis, the mutation in the base sequence is analyzed is also known (see, for example, Japanese Patent Application Laid-Open (JP-A) No. 2002-119291).

SUMMARY OF THE INVENTION

Problems of be Solved by the Invention

However, as mentioned above, there are various mutations as a mutation(s) of the ABCC2 gene. Therefore, in the PCR-RFLP method, it is necessary to carry out a PCR reaction, then collect the amplification products, and treat them with a restriction enzyme. Therefore, there may be a risk that the amplification products may contaminate the following reaction system, which may cause a false-positive or false-negative result. In addition, since the restriction enzyme treatment is carried out after the completion of PCR and then the resultant is electrophoresed, it may take a very long time until the detection. Furthermore, this method is hard to be automated due to complex operations thereof.

Under the present state as described above, it has been demanded to develop a technique for detecting a polymorphism in the ABCC2 gene.

An object of the present invention is to provide a probe for detecting a polymorphism which may make it possible to detect a polymorphism in the ABCC2 gene with a high sensitivity and easily, and a method of detecting a polymorphism by using the probe. Another object of the present invention is to provide a method of evaluating the efficacy of a drug by using the method of detecting a polymorphism. Yet another object of the present invention is to provide a reagent kit for detecting a polymorphism by using the probe for detecting a polymorphism.

Means for Solving the Problems

The present invention is as follows.
<1> A probe for detecting a polymorphism in the ABCC2 gene, the probe including one fluorescently labeled oligonucleotide selected from the group consisting of a P1 fluorescently labeled oligonucleotide and a P1' fluorescently labeled oligonucleotide, the P1 fluorescently labeled oligonucleotide having a sequence including the 207th to the 217th bases of the sequence indicated in SEQ ID NO:1 and having a length of from 11 bases to 60 bases, the sequence having an identity of at least 80% with respect to a base sequence having the same bases as SEQ ID NO:1 with the exception that the base corresponding to the 217th base in SEQ ID NO:1 is a cytosine, and the base corresponding to the 217th base of the sequence indicated in SEQ ID NO:1 being labeled with a fluorescent dye, and the P1' fluorescently labeled oligonucleotide having a sequence including the 207th to the 217th bases of the sequence indicated in SEQ ID NO:1 and having a length of from 11 bases to 60 bases, the sequence hybridizing under stringent conditions to a complementary strand of a base sequence having the same bases as SEQ ID NO:1 with the exception that the base corresponding to the 217th base in SEQ ID NO:1 is a cytosine, and the base corresponding to the 217th base of the sequence indicated in SEQ ID NO:1 being labeled with a fluorescent dye.

<2> The probe of <1>, including a P1-1 fluorescently labeled oligonucleotide or a P1'-1 fluorescently labeled oligonucleotide, the P1-1 fluorescently labeled oligonucleotide having a sequence including the 207th to the 217th bases of the sequence indicated in SEQ ID NO:1 and having a length of from 11 bases to 60 bases, the sequence having an identity of at least 80% with respect to a base sequence having the same bases as SEQ ID NO:1 with the exception that the base corresponding to the 217th base in SEQ ID NO:1 is a cytosine, the base corresponding to the 217th base of the sequence indicated in SEQ ID NO:1 being labeled with a fluorescent dye, and the oligonucleotide recognizing a polymorphism of the 207th base in SEQ ID NO:1, or the P1'-1 fluorescently labeled oligonucleotide having a sequence including the 207th to the 217th bases of the sequence indicated in SEQ ID NO:1 and having a length of from 11 bases to 60 bases, the sequence hybridizing under stringent conditions to a complementary strand of a base sequence having the same bases as SEQ ID NO:1 with the exception that the base corresponding to the 217th base in SEQ ID NO:1 is a cytosine, the base corresponding to the 217th base of the sequence indicated in SEQ ID NO:1 being labeled with a fluorescent dye, and the oligonucleotide recognizing a polymorphism of the 207th base in SEQ ID NO:1.

<3> The probe of <1> or <2>, wherein the 217th base labeled with a fluorescent dye is at a position of any one of 1st to 3rd positions from the 3' end of the fluorescently labeled oligonucleotide.

<4> The probe of any one of <1> to <3>, wherein the 217th base labeled with a fluorescent dye is at the 3' end of the fluorescently labeled oligonucleotide.

<5> The probe of any one of <1> to <4>, wherein the fluorescently labeled oligonucleotide emits fluorescence when the oligonucleotide is not hybridized to its target sequence; and the intensity of the fluorescence is decreased or increased when the oligonucleotide is hybridized to its target sequence.

<6> The probe of any one of <1> to <5>, wherein the fluorescently labeled oligonucleotide emits fluorescence when the oligonucleotide is not hybridized to its target sequence; and the intensity of the fluorescence is decreased when the oligonucleotide is hybridized to its target sequence.

<7> The probe of any one of <1> to <6>, wherein the fluorescently labeled oligonucleotide has a length of from 12 bases to 55 bases.

<8> The probe of any one of <1> to <7>, wherein the fluorescently labeled oligonucleotide has a length of from 15 bases to 45 bases.

<9> The probe of any one of <1> to <8>, wherein the fluorescently labeled oligonucleotide has a length of from 18 bases to 35 bases.

<10> The probe of any one of <1> to <9>, being a probe for melting curve analysis.

<11> The probe of any one of <1> to <10>, having a base sequence indicated in SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15 or SEQ ID NO:16.

<12> A method of detecting a polymorphism, wherein a polymorphism in the ABCC2 gene is detected by using the probe of any one of <1> to <11>.

<13> The method of detecting a polymorphism of <12>, which includes (I) contacting the probe of any one of <1> to <11> with a single-stranded nucleic acid in a sample and hybridizing the fluorescently labeled oligonucleotide and the single-stranded nucleic acid to obtain a hybrid;

(II) dissociating the hybrid by changing the temperature of the sample containing the hybrid, and measuring the change in the fluorescence signal caused by the dissociation of the hybrid;

(III) measuring, based on the change in the fluorescence signal, a Tm value which is a temperature at which the hybrid dissociates; and (IV) determining, based on the Tm value, whether the polymorphism in the ABCC2 gene on the single-stranded nucleic acid in the sample exists or not.

<14> The method of detecting a polymorphism of <13>, which further includes amplifying the nucleic acid before (I) or simultaneously with (I).

<15> The method of detecting a polymorphism of any one of <12> to <14>, which further includes detecting a polymorphism(s) in at least one selected from the group consisting of the MDR1 gene and the CYP3A5 gene by using at least one probe selected from the group consisting of a probe for detecting a polymorphism in the MDR1 gene and a probe for detecting a polymorphism in the CYP3A5 gene.

<16> A method of evaluating a drug efficacy or tolerance, which includes detecting a polymorphism in the ABCC2 gene by the method of detecting a polymorphism of any one of <12> to <15>, and evaluating tolerance to a drug or the efficacy of a drug based on the detected presence or absence of the polymorphism.

<17> A polymorphism detection reagent kit for detecting a polymorphism in the ABCC2 gene, which contains the probe of any one of <1> to <11>.

<18> The reagent kit of <17>, which further contains a primer for amplifying a region containing a sequence to which the P1 fluorescently labeled oligonucleotide hybridizes.

<19> The reagent kit of <17> or <18>, which further contains at least one probe selected from the group consisting of a probe for detecting a polymorphism in the MDR1 gene and a probe for detecting a polymorphism in the CYP3A5 gene.

Effect of the Invention

According to the present invention, a probe for detecting a polymorphism which may make it possible to detect a polymorphism in the ABCC2 gene with a high sensitivity and easily, and a method of detecting a polymorphism by using the probe may be provided. In addition, the present invention may provide a method of evaluating the efficacy of a drug by using the method of detecting a polymorphism. Further, the present invention may provide a reagent kit for detecting a polymorphism by using the probe for detecting a polymorphism.

DETAILED DESCRIPTION OF THE INVENTION

Figure 1A:
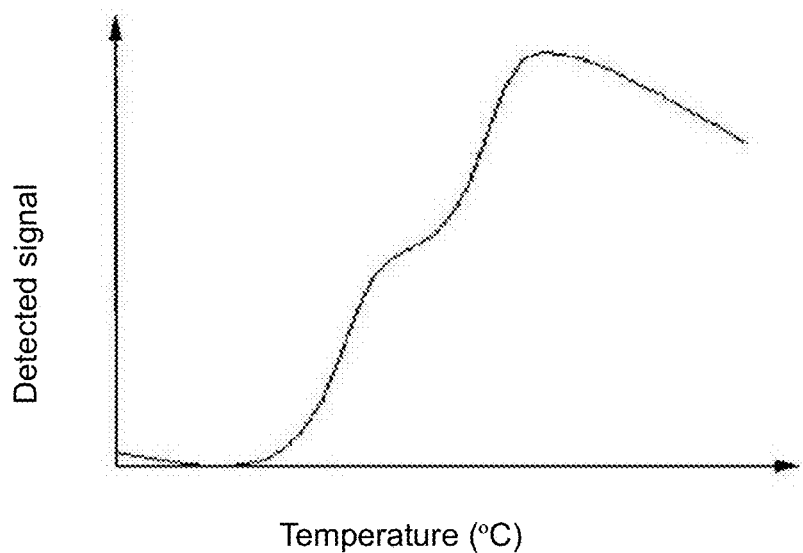
FIG. 1A is an example of a melting curve of a nucleic acid mixture.
Figure 1B:
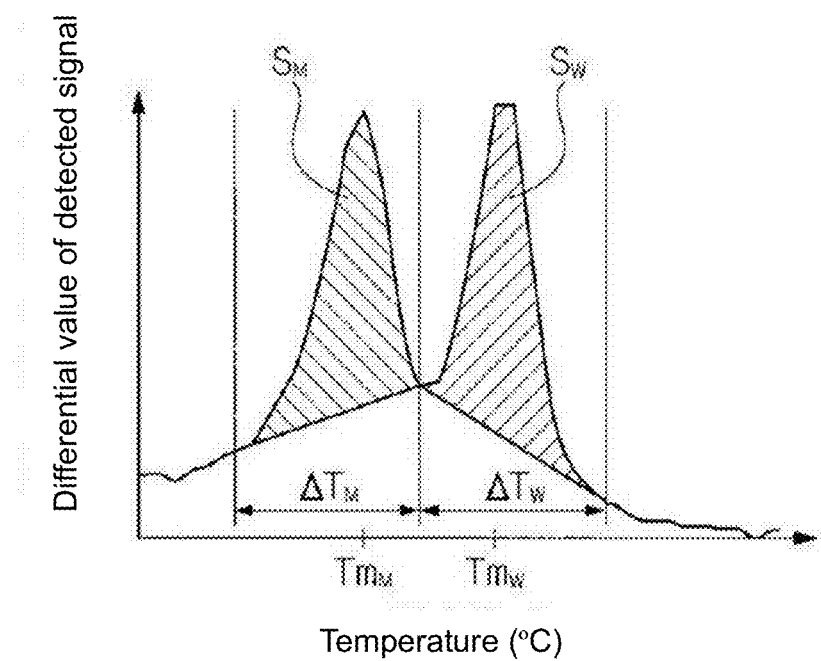
FIG. 1B is an example of a differential melting curve of a nucleic acid mixture.

The probe for detecting a polymorphism in the ABCC2 gene according to the present invention (hereinafter also simply referred to as "the probe") is a probe for detecting a polymorphism in the ABCC2 gene, the probe including one fluorescently labeled oligonucleotide selected from the group consisting of a P1 fluorescently labeled oligonucleotide and a P1' fluorescently labeled oligonucleotide, the P1 fluorescently labeled oligonucleotide having a sequence including the 207th to the 217th bases of the sequence indicated in SEQ ID NO:1 and having a length of from 11 bases to 60 bases, the sequence having an identity of at least 80% with respect to a base sequence having the same bases as SEQ ID NO:1 with the exception that the base corresponding to the 217th base in SEQ ID NO:1 is a cytosine, and the base corresponding to the 217th base of the sequence indicated in SEQ ID NO:1 being labeled with a fluorescent dye, and the P1' fluorescently labeled oligonucleotide having a sequence including the 207th to the 217th bases of the sequence indicated in SEQ ID NO:1 and having a length of from 11 bases to 60 bases, the sequence hybridizing under stringent conditions to a complementary strand of a base sequence having the same bases as SEQ ID NO:1 with the exception that the base corresponding to the 217th base in SEQ ID NO:1 is a cytosine, and the base corresponding to the 217th base of the sequence indicated in SEQ ID NO:1 being labeled with a fluorescent dye.

The method of detecting a polymorphism in the ABCC2 gene according to the present invention is a method which includes detecting a polymorphism in the ABCC2 gene by using at least one probe for detecting a polymorphism in the ABCC2 gene as described above.

The method of evaluating the efficacy of a drug according to the present invention is a method which includes detecting a polymorphism in the ABCC2 gene by the above-described method of detecting a polymorphism in the ABCC2 gene, and evaluating the tolerance to a drug or the efficacy of a drug based on the detected presence or absence of the polymorphism.

The reagent kit for detecting a polymorphism according to the present invention is a kit which contains the probe for detecting a polymorphism in the ABCC2 gene.

The ABCC2 gene in the present invention is already known, and the base sequence thereof is a sequence of NCBI Accession No. NC_000010.10 (101542463-101611662). The base sequence of SEQ ID NO:1 is a sequence of NCBI dbSNP Accession No. rs717620 (1-611), and this sequence corresponds to a part of the base sequence of the nucleic acid in the promoter region of the ABCC2 gene.

In the present invention, the descriptions of the base sequences of the sample nucleic acid in a sample to be detected and the probe or primer shall also apply to complementary base sequences thereof, respectively, unless otherwise specified. Further, when the description of a particular base sequence is applied to a complementary base sequence thereof, descriptions of base sequences recognized by the particular base sequence in the present invention should be applied provided that the recognition by the particular base sequence should be replaced with recognition by a complementary base sequence of the particular base sequence, within a range of the common general technical knowledge of those skilled in the art.

In the present invention, the term "Tm value" is defined as a temperature at which a double-stranded nucleic acid dissociates (dissociation temperature: Tm), and is generally defined as a temperature at which the absorbance at 260 nm has increased by 50% of the total increase in absorbance resulting from complete dissociation of the double-stranded nucleic acid. More specifically, when a solution containing a double-stranded nucleic acid such as a double-stranded DNA is heated, the absorbance at 260 nm of the double-stranded nucleic acid gradually increases. This is because the hydrogen bonds between both strands of the double-stranded DNA are broken by heating, thereby dissociating the double-stranded DNA into single-stranded DNAs (melting of DNA). When the double-stranded DNA has completely dissociated into single-stranded DNAs, the single-stranded DNAs exhibit an absorbance that is about 1.5 times the absorbance at the time of the initiation of the heating (i.e., the absorbance when the entire DNA is in the form of a double-stranded DNA), which serves as an indicator of the completion of the melting. The Tm value is defined based on this phenomenon. Tm values are defined based on such phenomena. The Tm values in the present invention mean temperatures at which the absorbance reaches 50% of the total increase between the initial absorbance and the final absorbance, unless otherwise noted.

In the present specification, the scope of the term "process" includes not only a discrete process, but also a process that cannot be clearly distinguished from another process as long as the expected effect of the process of interest is achieved.

In the present specification, any numerical range expressed using "to" refers to a range including the numerical values before and after "to" as the minimum and maximum values, respectively.

In a case in which the amount of a component that may be included in the composition is indicated in the present invention, when there are plural substances corresponding to the component in the composition, the indicated amount means the total amount of the plural substances present in the composition, unless specifically stated otherwise.

In the present invention, when the phrase "the first to third bases from the 3' end" is used in connection to an oligonucleotide sequence, it is assumed that the base at the 3' end of the oligonucleotide chain is the first base from the 3' end.

The present invention is described below.

<Probe for Detecting Polymorphism in ABCC2 Gene>

The probe for detecting a polymorphism in the ABCC2 gene according to the present invention (hereinafter also simply referred to as "the probe") is a probe for detecting a polymorphism in the ABCC2 gene, the probe including one fluorescently labeled oligonucleotide selected from the group consisting of a P1 fluorescently labeled oligonucleotide and a P1' fluorescently labeled oligonucleotide, the P1 fluorescently labeled oligonucleotide having a sequence including the 207th to the 217th bases of the sequence indicated in SEQ ID NO:1 and having a length of from 11 bases to 60 bases, the sequence having an identity of at least 80% with respect to a base sequence having the same bases as SEQ ID NO:1 with the exception that the base corresponding to the 217th base in SEQ ID NO:1 is a cytosine, and the base corresponding to the 217th base of the sequence indicated in SEQ ID NO:1 being labeled with a fluorescent dye, and the P1' fluorescently labeled oligonucleotide having a sequence including the 207th to the 217th bases of the sequence indicated in SEQ ID NO:1 and having a length of from 11 bases to 60 bases, the sequence hybridizing under stringent conditions to a complementary strand of a base sequence having the same bases as SEQ ID NO:1 with the exception that the base corresponding to the 217th base in SEQ ID NO:1 is a cytosine, and the base corresponding to the 217th base of the sequence indicated in SEQ ID NO:1 being labeled with a fluorescent dye.

One fluorescently labeled oligonucleotide selected from the group consisting of the P1 fluorescently labeled oligonucleotide and the P1' fluorescently labeled oligonucleotide of the present invention (hereinafter also referred to as "the P1 or P1' fluorescently labeled oligonucleotide") is a probe capable of detecting a polymorphism of the 207th base in the base sequence indicated in SEQ ID NO:1.

In addition, the P1 fluorescently labeled oligonucleotide and the P1' fluorescently labeled oligonucleotide of the present invention are, more specifically, a sequence including the 207th to the 217th bases of the sequence indicated in SEQ ID NO:1.

In the wild type of the ABCC2 gene, a base corresponding to the 207th base in the sequence indicated in SEQ ID NO:1 is a C (cytosine); but, in a mutant type thereof, the C has been mutated into a T (thymine) (this mutation is hereinafter referred to as "the C-24T mutation"). The base corresponds to the 207th base in the -428th to the 183rd bases of the ABCC2 gene.

The P1 fluorescently labeled oligonucleotide of the present invention needs to have a homology with respect to a base sequence having the same bases as SEQ ID NO:1 with the exception that the base corresponding to the 217th base in SEQ ID NO:1 is a C (cytosine).

More specifically, the P1 fluorescently labeled oligonucleotide of the present invention has an identity of not less than 80% with respect to a base sequence having the same bases as SEQ ID NO:1 with the exception that the base corresponding to the 217th base in SEQ ID NO:1 is a C (cytosine).

In addition, from the view point of the detection sensitivity, the P1 fluorescently labeled oligonucleotide of the present invention may have an identity of not less than 85%, an identity of not less than 90%, an identity of not less than 95%, an identity of not less than 96%, an identity of not less than 97%, an identity of not less than 98% or an identity of not less than 99%.

When the identities, in cases where the P1 fluorescently labeled oligonucleotide of the present invention is compared with the base sequence having the same bases as SEQ ID NO:1 with the exception that the base corresponding to the 217th base in SEQ ID NO:1 is a C (cytosine), are less than 80%, the detection sensitivity with respect to a sample nucleic acid including a mutant type of the ABCC2 gene will be lower.

In addition, the P1 fluorescently labeled oligonucleotide according to the present invention may be a fluorescently labeled oligonucleotide having a sequence including the 207th to the 217th bases of the sequence indicated in SEQ ID NO:1 and having a length of from 11 bases to 60 bases, the sequence having an identity of at least 80% with respect to a base sequence having the same bases as SEQ ID NO:1 with the exception that the base corresponding to the 217th base in SEQ ID NO:1 is a cytosine, the base corresponding to the 217th base of the sequence indicated in SEQ ID NO:1 being labeled with a fluorescent dye, and the oligonucleotide recognizing a polymorphism of the 207th base in SEQ ID NO:1 (i.e., the P1-1 fluorescently labeled oligonucleotide).

In this fluorescently labeled oligonucleotide, the detection sensitivity to a sample nucleic acid including the mutant type of the ABCC2 gene tends to be higher.

The P1' fluorescently labeled oligonucleotide in the present invention needs to be able to hybridize under stringent conditions to a complementary strand of a base sequence having the same bases as SEQ ID NO:1 with the exception that the base corresponding to the 217th base in SEQ ID NO:1 is a C (cytosine).

The hybridization may be carried out according to a known method or a method corresponding thereto, such as a method as described in Molecular Cloning 3rd (J. Sambrook et al., Cold Spring Harbor Lab. Press, 2001). This document is incorporated herein by reference.

The term "stringent conditions" means conditions in which specific hybrids are formed, but non-specific hybrids are not formed. Typical examples of the stringent conditions include, for example, conditions in which the hybridization is carried out at a potassium concentration from about 25 mM to about 50 mM and a magnesium concentration from about 1.0 mM to about 5.0 mM. One example of the conditions of the present invention is conditions in which the hybridization is carried out in Tris-HCl (pH 8.6), 25 mM KCl, and 1.5 mM $MgCl_2$, but examples of the conditions of the present invention are not limited thereto. Other examples of the stringent conditions are described in Molecular Cloning 3rd (J. Sambrook et al., Cold Spring Harbor Lab. Press, 2001). This document is incorporated herein by reference. Those skilled in the art may readily choose such conditions by changing the hybridization reaction and/or the salt concentration of the hybridization reaction solution.

The P1' fluorescently labeled oligonucleotide according to the present invention may be a fluorescently labeled oligonucleotide having a sequence including the 207th to the 217th bases of the sequence indicated in SEQ ID NO:1 and having a length of from 11 bases to 60 bases, the sequence hybridizing under stringent conditions to a complementary strand of a base sequence having the same bases as SEQ ID NO:1 with the exception that the base corresponding to the 217th base in SEQ ID NO:1 is a cytosine, the base corresponding to the 217th base of the sequence indicated in SEQ ID NO:1 being labeled with a fluorescent dye, and the oligonucleotide recognizing a polymorphism of the 207th base in SEQ ID NO:1 (i.e., the P1'-1 fluorescently labeled oligonucleotide).

Since this fluorescently labeled oligonucleotide has not only the particular base sequence but also a function of recognizing a polymorphism of the 207th base in SEQ ID NO:1, the detection sensitivity with respect to a sample nucleic acid including the mutant type of the ABCC2 gene tends to be higher.

Furthermore, the P1 or P1' fluorescently labeled oligonucleotide in the present invention encompasses a fluorescently labeled oligonucleotide having a sequence wherein a base(s) have been inserted to, deleted from and/or substituted in the P1 or P1' fluorescently labeled oligonucleotide.

The fluorescently labeled oligonucleotide having a sequence wherein a base(s) have been inserted, deleted and/or substituted is not particularly limited, as long as the oligonucleotide exhibits an effect similar to that of the P1 or P1' fluorescently labeled oligonucleotide; and, in cases where a base(s) have been inserted, deleted and/or substituted, the position(s) of the insertion(s), deletion(s) and/or substitution(s) are not particularly limited. The number of bases that have been inserted, deleted and/or substituted may be, for example, 1 base, or 2 or more bases, such as from 1 base to 10 bases and from 1 base to 5 bases, although varying depending on the total length of the fluorescently labeled oligonucleotide.

In particular, the P1 or P1' fluorescently labeled oligonucleotide in the present invention encompasses a fluorescently labeled oligonucleotide having a sequence which may be obtained by substituting a base(s) of the P1 or P1' fluorescently labeled oligonucleotide.

The fluorescently labeled oligonucleotide having a sequence which may be obtained by substituting a base(s) is not particularly limited, as long as the oligonucleotide exhibits an effect similar to that of the P1 or P1' fluorescently labeled oligonucleotide; and the position(s) of the substitution(s) are not particularly limited. For example, in view of In Table 1, the base corresponding to the 207th base of SEQ ID NO:1 is shown with a lower case letter; and this table shows not only oligonucleotides in cases where their bases corresponding to the 207th base of SEQ ID NO:1 are an A, a G, a T or a C, but also the Tm values of the hybrids which are each formed by these fluorescently labeled oligonucleotides. The underlined bases represent bases which are different from the sequence indicated in SEQ ID NO:1 since a mutation(s) has been introduced.

The Tm values were calculated by using MeltCalc© 99 FREE (meltcalc.com/) and under the set conditions of: Oligoconc. [μM] of 0.2 and Na eq. [mM] of 50.

TABLE 1

| sequence (5'→3') | mer | Tm mt | Tm WT | ΔX | SEQ ID NO |
|---|---|---|---|---|---|
| TCTGGAACgAAGACTCTTC | 19 | 50.2 | 43.2 | 7.0 | 4 |
| CATGATTCCTGGACTGCGTCTGGAACaAAGACTCTTC | 37 | 65.6 | 62.3 | 3.3 | 5 |
| CATGATTCCTGGACTGCGTCTGGAACaAAGACTCTTCTATTAATATGATTGTGTTGT | 57 | 67.4 | 65.4 | 2.0 | 6 |
| TCTGCAACgAAGACTCTTC | 19 | 30.1 | 39.4 | 9.3 | 7 |
| AATGATACCTGGACTGCGTCTGGAACaAAGACTCTTC | 37 | 61.7 | 51.8 | 9.9 | 8 |
| CATGATTCCTGGACTGCGTCTGGAACaAAGACTCTTCTAGGAATATGATTGTGTTGT | 57 | 66.7 | 64.6 | 2.1 | 9 |
| CtAAGACTCTTC | 12 | 16.8 | 12.7 | 4.1 | 10 |
| CcAAGACTCTTC | 12 | 12.5 | 9.7 | 2.8 | 11 |

※ΔX is the difference between a Tm value in case of mt (mutant type) and a Tm value in case of WT (Wild Type).

the detection sensitivity, a substitution(s) of a base(s) other than the 207th to the 217th bases of the sequence indicated in SEQ ID NO:1 may be included. The number of bases that have been substituted may be, for example, 1 base, or 2 or more bases, such as from 1 base to 5 bases and from 1 base to 3 bases, although varying depending on the total length of the fluorescently labeled oligonucleotide.

The P1 or P1' fluorescently labeled oligonucleotide of the present invention needs to have a length of from 11 mer to 60 mer. When the P1 or P1' fluorescently labeled oligonucleotide has a length of 10 mer or less or a length of 61 mer or more, the sensitivity for detecting a polymorphism in the ABCC2 gene will be decreased.

In addition, the P1 or P1' fluorescently labeled oligonucleotide of the present invention may have a length of from 12 mer to 55 mer, a length of from 15 mer to 45 mer, or a length of from 18 mer to 35 mer. By using the range of from 12 mer to 55 mer, for example, the detection sensitivity tends to be higher.

By varying the base length of the P1 or P1' fluorescently labeled oligonucleotide, for example, the Tm value, which is a dissociation temperature of a hybrid formed by the P1 or P1' fluorescently labeled oligonucleotide and its complementary strand (target sequence), may be adjusted to a desired value.

Examples of the base sequence of the P1 or P1' fluorescently labeled oligonucleotide in the present invention are shown in Table 1 below, but the present invention is not limited to these.

In the present invention, the difference between a Tm value in a case where the P1 or P1' fluorescently labeled oligonucleotide is hybridized with a DNA having a base sequence that is completely complementary to the base sequence of the P1 or P1' fluorescently labeled oligonucleotide (the Tm (mt) in Table 1) and a Tm value in a case where the P1 or P1' fluorescently labeled oligonucleotide is hybridized with a DNA having a base sequence that is complementary to the base sequence of the P1 or P1' fluorescently labeled oligonucleotide with the exception that its base corresponding to the 207th base of SEQ ID NO:1 is non-complementary to the base sequence of the P1 or P1' fluorescently labeled oligonucleotide (Tm (WT) in Table 1) may be, for example, 2.0° C. or more, 3.0° C. or more, 5.0° C. or more, and 7.0° C. or more. When the difference between the Tm values is 2.0° C. or more, for example, a mutation of the 207th base in SEQ ID NO:1 may be detected with a higher sensitivity.

Further, the P1 or P1' fluorescently labeled oligonucleotide of the present invention needs to be labeled with a fluorescent dye at its base corresponding to the 217th base.

In the P1 or P1' fluorescently labeled oligonucleotide, the fluorescently labeled base corresponding to the 217th base may exist at a position of any one of 1st to 3rd positions from the 3' end of the P1 or P1' fluorescently labeled oligonucleotide. Alternatively, the fluorescently labeled base may exist at the 3' end of the P1 or P1' fluorescently labeled oligonucleotide. Thereby, for example, the sensitivity for detecting a polymorphism is further improved. In addition, the P1 or P1' fluorescently labeled oligonucleotide may be obtained with good productivity.

The fluorescently labeled oligonucleotide of the present invention may be a fluorescently labeled oligonucleotide in which the fluorescence intensity at the time when the oligonucleotide is hybridized to its target sequence is decreased (quenched) or increased as compared to the fluorescence intensity at the time when the oligonucleotide is not hybridized to its target sequence. In particular, the fluorescently labeled oligonucleotide of the present invention may be a fluorescently labeled oligonucleotide in which the fluorescence intensity at the time when the oligonucleotide is hybridized to its target sequence is decreased as compared to the fluorescence intensity at the time when the oligonucleotide is not hybridized to its target sequence.

A probe that uses the "fluorescence quenching phenomenon" as described above is generally referred to as a guanine quenching probe, and it is known as Q PROBE®. Among such probes, an oligonucleotide which has been designed so that its 3' or 5' end is a cytosine (C) and which has been labeled with a fluorescent dye so that the fluorescence emission is reduced when the C at the 3' or 5' end comes close to a guanine (G) is especially preferable. By using such a probe, the labeled oligonucleotide sufficiently suppresses elongation of the probe itself by a gene amplification reaction. As described below, a DNA for which the presence or absence of a mutation should be detected (target DNA) may be prepared using a gene amplification method such as PCR. When the fluorescent-labeled oligonucleotide that has a phosphate group added to its 3' end is used, the amplification reaction can be carried out even in the presence of the oligonucleotide in a reaction solution of the amplification reaction.

A similar effect can be obtained also by adding a labeling substance (a fluorescent dye) as described above to the 3' end.

Specific examples of the oligonucleotide which has the above-described base sequence and in which the C at its 3' end has been labeled with a fluorescent dye are shown below (the base indicated by a capital letter each represents a mutated site, and the "(TAMRA)" corresponds to the above-described fluorescent dye). However, the fluorescently labeled oligonucleotide in the present invention is not limited to those described below.

TABLE 2

| Probe | sequence(5'→3') | (mer) | SEQ ID NO |
|---|---|---|---|
| 3T-ABCC2-C-24T-mt-F2 | tctggaacAaagactcttc-(TAMRA) | 19 | 12 |
| 3T-ABCC2-C-24T-WT-Fa | tctagaacGaagactcttc-(TAMRA) | 19 | 13 |
| 3T-ABCC2-C-24T-mt-Fb | ggactgcgtctggaacAaagactcttc-(TAMRA) | 27 | 14 |
| 3T-ABCC2-C-24T-mt-Fc | ttcctgaaccgcgtctggaacAaagactcttc-(TAMRA)-t | 32 | 15 |
| 3T-ABCC2-C-24T-mt-Fd | ttcctgaaccAcgtctggaacGaagactcttc-(TAMRA) | 32 | 16 | hybridization and dissociation of the probe may be readily checked by the change in its signal.

A known detection method other than the detection method using a Q PROBE® may also be applied. Examples of such a detection method include a TAQ-MAN probe method, a a hybridization probe method, a molecular beacon method, and a MGB probe method.

The fluorescent dye is not particularly limited, and examples of the fluorescent dye include fluorescein, phosphor, rhodamine and polymethine dye derivatives. Examples of commercially available products of such fluorescent dyes include Pacific Blue, BODIPY FL, FluorePrime, Fluoredite, FAM, Cy3 and Cy5, and TAMRA.

The detection conditions of the fluorescent-labeled oligonucleotide are not particularly limited, and may be decided, as appropriate, in accordance with the fluorescent dye to be used. For example, Pacific Blue can be detected at a detection wavelength of from 445 nm to 480 nm, TAMRA can be detected at a detection wavelength of from 585 nm to 700 nm, and BODIPY FL can be detected at a detection wavelength of from 520 nm to 555 nm.

By using a probe having such a fluorescent dye, hybridization and dissociation of the probe can be readily confirmed based on a change in fluorescence signal thereof. Attachment of a fluorescent dye to the oligonucleotide may be carried out according to an ordinary method, such as a method described in JP-A No. 2002-119291.

It should be noted that, in the present invention, the same fluorescent dye may be used, or alternatively, different fluorescent dyes may be used to label one or more of the oligonucleotide.

In addition, the fluorescent-labeled oligonucleotide may have, for example, a phosphate group added to its 3' end. Addition of a phosphate group to the 3' end of the fluorescent- The P1 fluorescently labeled oligonucleotide may be used as an ABCC2 gene probe for detecting a polymorphism in the ABCC2 gene, particularly the C-24T mutation.

In addition, the probe for detecting a polymorphism in the ABCC2 gene may be used as a probe for melting curve analysis.

The P1 fluorescently labeled oligonucleotide according to the present invention may be produced according to a conventional method known as a method for synthesizing an oligonucleotide, such as a method as described in JP-A No. 2002-119291, except that bases are used so that the base corresponding to the 217th base in the base sequence indicated in SEQ ID NO:1 is a cytosine and the base corresponding to the 217th base is labeled with a fluorescent dye.

<Primer>

In the below-described method of detecting a polymorphism in the ABCC2 gene, primers are used in amplifying a sequence having an ABCC2 gene polymorphism to be detected by a PCR method.

The primer that may be used in the present invention is not particularly limited, as long as they are capable of amplifying a nucleic acid that contains the base corresponding to the 207th base of the sequence indicated in SEQ ID NO:1, which is a desired ABCC2 gene polymorphism site to be detected.

The primer to be applied to the PCR method is not particularly limited, as long as it is capable of amplifying a region to which the probe of the present invention may be hybridized. Such a primer may be properly designed based on the base sequence indicated in SEQ ID NO:1 by those skilled in the art. The length and Tm value of the primer may be a length of from 12 mer to 40 mer and a value of from 40° C. to 70° C., or a length of from 16 mer to 30 mer and a value of from 55° C. to 60° C.

The lengths of individual primers in a primer set do not need to be the same, although the Tm values of these primers are preferably approximately the same (or the difference between the Tm values of these primers is preferably within 5° C.).

Examples of the primers that may be used for amplifying a base sequence containing a region to which the probe of the present invention in the polymorphism detection method of the present invention may be hybridized are shown below. These are exemplary and therefore the present invention is not limited to these.

The primer for detecting a polymorphism of the 207th base of the sequence indicated in SEQ ID NO:1 preferably includes at least one oligonucleotide selected from the group consisting of the below-described P2, P2', P3 and P3' oligonucleotides.

The P2 oligonucleotide has an identity of at least 80% with respect to a base sequence including the 172nd to the 194th bases of the base sequence indicated in SEQ ID NO:1 and has a length of from 23 bases to 60 bases; the P2' oligonucleotide hybridizes under stringent conditions to a complementary strand of a base sequence including the 172nd to the 194th bases of the base sequence indicated in SEQ ID NO:1 and has a length of from 23 bases to 60 bases; the P3 oligonucleotide has an identity of at least 80% with respect to a complementary strand of a base sequence including the 265th to the 294th bases of the base sequence indicated in SEQ ID NO:1 and has a length of from 30 bases to 60 bases; and the P3' oligonucleotide hybridizes under stringent conditions to a base sequence including the 265th to the 294th bases of the base sequence indicated in SEQ ID NO:1 and has a length of from 30 bases to 60 bases.

The P2 oligonucleotide may be an oligonucleotide which has an identity of at least 80% with respect to a base sequence including the 172nd to the 194th bases of the base sequence indicated in SEQ ID NO:1 and having a length of from 23 bases to 60 bases, and which may be used for amplifying a region containing the 207th base in SEQ ID NO:1. The P2' oligonucleotide may be an oligonucleotide which may hybridize under stringent conditions to a complementary strand of a base sequence including the 172nd to the 194th bases of the base sequence indicated in SEQ ID NO:1 and having a length of from 23 bases to 60 bases, and which may be used for amplifying a region containing the 207th base in SEQ ID NO:1. Furthermore, the P2 oligonucleotide or the P2' oligonucleotide may be an oligonucleotide having a sequence wherein a base(s) has been inserted to, deleted from and/or substituted in the P2 oligonucleotide or the P2' oligonucleotide.

The P3 oligonucleotide may be an oligonucleotide which has an identity of at least 80% with respect to a complementary strand of a base sequence including the 265th to the 294th bases of the base sequence indicated in SEQ ID NO:1 and having a length of from 30 bases to 60 bases, and which may be used for amplifying a region containing the 207th base in SEQ ID NO:1. The P3' oligonucleotide may be an oligonucleotide which may hybridize under stringent conditions to a base sequence including the 265th to the 294th bases of the base sequence indicated in SEQ ID NO:1 and having a length of from 30 bases to 60 bases, and which may be used for amplifying a region containing the 207th base in SEQ ID NO:1. Furthermore, the P3 oligonucleotide or the P3' oligonucleotide may be an oligonucleotide having a sequence wherein a base(s) has been inserted to, deleted from and/or substituted in the P3 oligonucleotide or the P3' oligonucleotide.

The hybridization may be carried out according to a method as described above, and, as the stringent conditions, conditions similar to the above-described conditions may be applied. The range of the identity, and an insertion, a deletion and a substitution to be applied may also be similar to those as described in the section which describes the probe.

Examples of the primers that may be used for amplifying a region containing the 207th base in SEQ ID NO:1 in the polymorphism detection method of the present invention are shown below.

TABLE 3

| primer | sequence (5'→3') | (mer) | SEQ ID NO |
|---|---|---|---|
| ABCC2-C-24T-F1 | cttctccagcatgattcctggac | 23 | 17 |
| ABCC2-C-24T-R1 | atcagaatggtagataattcctgttccact | 30 | 18 |

In order to detect the polymorphism of the 207th base in SEQ ID NO:1, it is more preferable to use the P2 oligonucleotide and the P3 oligonucleotide, or the P2' oligonucleotide and the P3' oligonucleotide as a set of paired primers.

The method of detecting a polymorphism is not particularly limited, as long as it is a method in which the fluorescently labeled nucleotide as described above is used as a probe. As an example of the polymorphism detection method in which the fluorescently labeled nucleotide as described above is used as a probe, a method of detecting a polymorphism using Tm analysis is described below.

<Polymorphism Detection Method>

The method of detecting a polymorphism in the ABCC2 gene according to the present invention is a method of detecting a polymorphism in the ABCC2 gene which includes detecting a polymorphism in the ABCC2 gene by using at least one probe for detecting a polymorphism in the ABCC2 gene as described above.

The method of detecting a polymorphism of the present invention may include at least one probe for detecting a polymorphism as described above, and this may make it possible to detect a polymorphism(s) in the ABCC2 gene easily and with a high sensitivity.

In addition, the method of detecting a gene mutation according to the present invention may be employed as a method of detecting a gene mutation in various human genes, and may include the below-described processes (I) to (IV), and may include the below-described process (V). The method of detecting a gene mutation according to the present invention has a feature of using the above-described probe, and other configurations, conditions and the like are not particularly limited by the description below.

Process (I): contacting the fluorescent-labeled probe with a single-stranded nucleic acid in a sample, to obtain a hybrid.

Process (II): dissociating the hybrid by changing the temperature of the sample containing the hybrid, and measuring a change in fluorescence signal due to the dissociation of the hybrid.

Process (III): measuring a Tm value, which is the dissociation temperature of the hybrid, based on the change in fluorescence signal.

Process (IV): detecting the presence of the ABCC2 gene mutation on the single-stranded nucleic acid in the sample, based on the Tm value.

Process (V): determining the abundance ratio of single-stranded nucleic acid having the gene mutation in the total single-stranded nucleic acids contained in the sample, based on the presence of the gene mutation.

Furthermore, the method according to the present invention may further include amplifying the nucleic acid before the obtainment of the hybrid in the process (I) or simultaneously with the obtainment of the hybrid in the process (I), in addition to the processes (I) to (IV) or in addition to the processes (I) to (V).

The measurement of the Tm value in the process (III) may include not only measuring the dissociation temperature of the hybrid, but also measuring the differential values of the fluorescence signal that changes according to the temperature when the hybrid is melted.

In the present invention, the nucleic acid in the sample may be a single-stranded nucleic acid or a double-stranded nucleic acid. In a case in which the nucleic acid is a double-stranded nucleic acid, the method may include, for example, melting (dissociating) the double-stranded nucleic acid in the sample into single-stranded nucleic acids by heating before being hybridized with the fluorescent-labeled probe. The dissociation of a double-stranded nucleic acid into single-stranded nucleic acids enables hybridization with the fluorescent-labeled probe.

In the present invention, the nucleic acid contained in the sample to be detected may be, for example, a nucleic acid originally contained in a biological sample, or an amplification product obtained by amplifying a region of the gene of interest that contains a mutated site(s) of the ABCC2 gene by PCR or the like using a nucleic acid originally contained in a biological sample as a template with a view to improving the detection accuracy. The length of the amplification product is not particularly limited, and may be, for example, a length of from 50 mer to 1000 mer, or a length of from 80 mer to 200 mer. Furthermore, the nucleic acid in the sample may be, for example, a cDNA that has been synthesized from RNAs derived from a biological sample (e.g., total RNAs, mRNAs, etc.) by RT-PCR (Reverse Transcription PCR).

In the present invention, the addition ratio (molar ratio) of the probe according to the present invention relative to the nucleic acids in the sample is not particularly limited. The amount of the probe to be added may be, for example, no more than 1 times (by mol) the amount of DNAs in the sample. From the viewpoint of ensuring a sufficient detection signal, the addition ratio of the probe according to the present invention to be added relative to the nucleic acids in the sample (in a molar ratio) may be 0.1 or lower.

The "nucleic acids in the sample" may be, for example, a total of nucleic acids to be detected that have the gene mutation to be detected and nucleic acids, other than the nucleic acids to be detected, that do not have the gene mutation, or a total of amplification products containing a detection target sequence having the gene mutation to be detected and amplification products containing a sequence, other than the detection target sequence, that does not have the gene mutation. Although the ratio of the nucleic acid to be detected relative to nucleic acids in the sample is usually unknown in advance, the consequential addition ratio of the probe relative to the nucleic acids to be detected (or the amplification products containing a sequence to be detected) (in a molar ratio) may be 10 or lower. The addition ratio of the probe relative to the nucleic acids to be detected (or the amplification products containing a sequence to be detected) (in a molar ratio) may be 5 or lower, or 3 or lower. The lower limit of the ratio is not particularly limited, and may be, for example, 0.001 or higher, 0.01 or higher, or 0.1 or higher.

The above-described addition ratio of the fluorescent-labeled probe according to the present invention relative to DNAs may be, for example, a molar ratio relative to double-stranded nucleic acids or a molar ratio relative to single-stranded nucleic acids.

In the present invention, the measurement of a change in the signal caused by a temperature change for determining a Tm value may be carried out by measuring the absorbance at 260 nm on the basis of the principle described above. However, the measurement may be carried out by measuring a signal which is based on a signal from the label attached to the fluorescent-labeled probe, and which varies in accordance with the degree of the formation of a hybrid of a single-stranded DNA and the probe. Therefore, the above-described fluorescent-labeled oligonucleotide may be used as the fluorescent-labeled probe. Examples of the fluorescent-labeled P1, P1-1, P1', or P1'-1 oligonucleotide (hereinafter sometimes collectively referred to as "fluorescent-labeled oligonucleotide") include a fluorescent-labeled oligonucleotide of which the fluorescence intensity when the oligonucleotide is hybridized with a target sequence thereof is decreased (quenched) as compared to the fluorescence intensity when the oligonucleotide is not hybridized with the target sequence thereof, and a fluorescent-labeled oligonucleotide of which the fluorescence intensity when the oligonucleotide is hybridized with a target sequence thereof is increased as compared to the fluorescence intensity when the oligonucleotide is not hybridized with the target sequence thereof.

The former fluorescent-labeled oligonucleotide does not show a fluorescence signal or only a weak fluorescence signal when the fluorescent-labeled oligonucleotide forms a hybrid (a double-stranded DNA) with the sequence to be detected; however, the fluorescent-labeled oligonucleotide becomes to show a fluorescence signal or shows an increased fluorescence signal when the fluorescent-labeled oligonucleotide is dissociated by heating.

The latter fluorescent-labeled oligonucleotide shows a fluorescence signal when the fluorescent-labeled oligonucleotide forms a hybrid (a double-stranded DNA) with the sequence to be detected; however, the fluorescent-labeled oligonucleotide shows a decreased fluorescence signal or ceases to show a fluorescent signal when the fluorescent-labeled oligonucleotide is dissociated by heating. Therefore, similar to the measurement of the absorbance at 260 nm described above, the progress of melting can be monitored, and the Tm value can be determined by detecting the change in the fluorescence signal from the fluorescent label under the conditions specific to the fluorescent label (for example, the fluorescence wavelength thereof).

The method for detecting the change in the signal based on a signal from the fluorescent dye in the polymorphism detection method according to the present invention is described below by way of specific examples. The polymorphism detection method according to the present invention has a feature of using the fluorescent-labeled polymorphism detection probe, and other processes and conditions of the method are not limited in any way.

The sample containing a nucleic acid that serves as a template for nucleic acid amplification is not particularly limited as long as the sample contains a nucleic acid, particularly the ABCC2 gene. Examples of such a sample include a sample that is derived from or can be derived from any biological source, examples of which include: a tissue such as colon or lung; a hemocyte such as a leukocyte cell; whole blood; plasma; a sputum; a suspension of oral mucosa; a somatic cell of nail, hair or the like; a germ cell; milk; ascitic fluid; a paraffin-embedded tissue; gastric juice; a gastric lavage fluid; urine; peritoneal fluid; amniotic fluid; and a cell culture. The method for sampling the sample, the method for preparing the sample containing a nucleic acid, and the like are not limited, and, conventional methods known in the art may be employed therefor. A nucleic acid obtained from such a biological source may be directly used as the template, or may be used after the sample has been subjected to pretreatment that modifies the properties of the sample.

For example, in a case in which whole blood is used as the sample, the isolation of genomic DNA from the whole blood may be carried out by a conventional method known in the art. For example, a commercially available genomic DNA isolation kit (trade name: GFX GENOMIC BLOOD DNA PURIFICATION KIT, available from GE Healthcare Biosciences), etc. may be used.

Next, a fluorescent-labeled polymorphism detection probe including the fluorescent-labeled oligonucleotide is added to the sample containing an isolated genomic DNA.

The fluorescent-labeled probe may be added to a liquid sample containing an isolated genomic DNA, or may be mixed with a genomic DNA in an appropriate solvent. The solvent is not particularly limited, and examples of the solvent include conventional solvents known in the art, such as: a buffer solution such as Tris-HCl; a solvent containing at least one of KCl, $MgCl_2$, $MgSO_4$, or glycerol; and a PCR reaction solution.

The timing of adding the fluorescent-labeled probe is not particularly limited. For example, in a case in which an amplification process such as PCR described below is carried out, the fluorescent-labeled probe may be added to the PCR amplification products after the amplification process is carried out, or may be added before the amplification process is carried out.

In a case in which the fluorescent-labeled probe is added before an amplification process such as PCR is carried out, for example, a fluorescent dye or a phosphate group may have been added to the 3' end of the probe, as described above.

The method of amplifying a nucleic acid may be, for example, a method in which a polymerase is employed. Examples of thereof include a PCR method, an ICAN method, a LAMP method, and an NASBA method. In a case in which the amplification is carried out by a method in which a polymerase is employed, the amplification may be carried out in the presence of the fluorescent-labeled probe according to the present invention. Those skilled in the art would be able to easily adjust the reaction conditions of the amplification and the like in accordance with the fluorescent-labeled probe and the polymerase to be used. In a case in which the amplification is carried out in the presence of the fluorescent-labeled probe according to the present invention, a gene mutation can be detected by only analyzing the Tm value of the fluorescent-labeled probe after the amplification of the nucleic acid is carried out, and, therefore, it is not necessary to separate the amplification product after completion of the reaction. Thus, contamination by the amplification product does not occur. In addition, since the detection can be carried out by the same apparatus as the apparatus required for the amplification, conveyance of a vessel is unnecessary, and automatization of the process is facilitated.

The DNA polymerase to be used in the PCR method may be selected, without particular limitation, from DNA polymerases that are usually used for PCR. Examples of the DNA polymerase include GENE TAQ (trade name, manufactured by NIPPON GENE CO., LTD.), PRIMESTAR MAX DNA POLYMERASE (trade name, manufactured by Takara Bio Inc.), and a Taq polymerase.

The amount of the polymerase to be used is not particularly limited as long as a usually-applied polymerase concentration is provided. For example, in a case in which a Taq polymerase is used, the concentration of the Taq polymerase may be, for example, a concentration of from 0.01 U to 100 U relative to 50 pl of the reaction solution. In this range, for example, the sensitivity of the detection of polymorphism in the ABCC2 gene tends to be increased The PCR method may be carried out under the conditions appropriately selected from usually-employed conditions.

When the amplification is carried out, the amplification may be monitored using real-time PCR so that the copy number of the DNA (a sequence to be detected) contained in the sample can be measured. In other words, the proportion of probes forming hybrids is increased as the amplification of the DNA (a sequence to be detected) by PCR proceeds, thereby changing the fluorescence intensity. By monitoring the change in the fluorescence intensity, the copy number and/or the abundance ratio of the sequence to be detected (either a normal DNA or a mutant DNA) contained in the sample can be obtained.

In the polymorphism detection method according to the present invention, the fluorescent-labeled oligonucleotide and a single-stranded nucleic acid in the sample are brought into contact with each other, thereby allowing hybridization thereof. The single-stranded nucleic acid in the sample can be prepared by, for example, dissociating the PCR amplification products obtained in the above-described manner.

The heating temperature employed for dissociation of the PCR amplification products (the heating temperature in the dissociation process) is not particularly limited as long as it is a temperature at which the amplification products can be dissociated. For example, the heating temperature may be in the range of from 85° C. to 95° C. The heating time is not particularly limited, either. The heating time may be, for example, in the range of from 1 second to 10 minutes, or from 1 second to 5 minutes.

The hybridization of the dissociated single-stranded DNA and the fluorescent-labeled oligonucleotide may be carried out by, for example, decreasing, after the dissociation process, the temperature from the heating temperature employed in the dissociation process. The temperature condition for the hybridization may be, for example, in the range of from 40° C. to 50° C.

The volume and concentration of each component in the reaction solution in the hybridization process are not particularly limited. In regard to specific examples thereof, the concentration of DNAs in the reaction solution may be, for example, a concentration of from 0.01 µM to 1 µM, or a concentration of from 0.1 µM to 0.5 µM. The concentration of the fluorescent-labeled oligonucleotide may be, for example, in a range in which the above-described addition ratio relative to DNAs is satisfied, and may be, for example, a concentration of from 0.001 µM to 10 µM, or a concentration of from 0.001 µM to 1 µM.

The resultant hybrid of the single-stranded DNA and the fluorescent-labeled oligonucleotide is gradually heated, and a change in fluorescence signal caused by the temperature increase is measured. For example, in the case of using Q PROBE®, the fluorescence intensity in the state of being hybridized with the single-stranded DNA is decreased (or quenched) as compared to the fluorescence intensity in the dissociated state. Therefore, for example, the hybrid emitting decreased fluorescence or the quenched hybrid may be gradually heated, and an increase in fluorescence intensity caused by the temperature increase may be measured.

The temperature range in which the change in fluorescence intensity is measured is not particularly limited, and the initial temperature may be, for example, a temperature of from room temperature to 85° C., or a temperature of from 25° C. to 70° C. The final temperature may be, for example, a temperature of from 40° C. to 105° C. The temperature increase rate is not particularly limited, either, and may be, for example, in the range of from 0.1° C./sec to 20° C./sec, or in the range of from 0.3° C./sec to 5° C./sec.

Next, the change in the signal is analyzed to determine the Tm value. More specifically, the Tm value may be determined by calculating a differential value at each temperature (−d (Fluorescence Intensity)/dt) from the fluorescent intensity obtained, and taking the temperature at which the differential value takes the lowest value as the Tm value. The Tm value may alternatively be determined as the point at which the increase in fluorescence intensity per unit time ((Increase in Fluorescence Intensity)/t) takes the largest value. On the contrary, in a case in which a probe of which signal intensity is increased by the formation of the hybrid, rather than a quenching probe, is used as the fluorescent-labeled probe, the signal analysis and the determination of the Tm value may be carried out by measuring a decrease in fluorescence intensity.

In the present invention, a change in fluorescence signal caused by a temperature increase (preferably an increase in fluorescence intensity) may be measured while heating the hybrid as described above. However, instead of this method, the measurement of a change in signal may alternatively be carried out, for example, in the course of hybrid formation. In other words, the temperature of the sample, to which the probe has been added, may be decreased, and a change in fluorescence signal caused by the temperature decrease may be measured in the course of hybrid formation.

For example, in case in which Q PROBE® is used, the fluorescence intensity is high when the probe is added to the sample since the probe is in the dissociated state. However, when the hybrid is formed by temperature decrease, the fluorescence is decreased (or quenched). Therefore, for example, a decrease in fluorescence intensity caused by temperature decrease may be measured while gradually decreasing the temperature of the heated sample.

On the other hand, in a case in which a probe of which signal is increased by hybrid formation is used, the fluorescence intensity is low (or quenched) when the probe is added to the sample since the probe is in the dissociated state. However, when the hybrid is formed by temperature decrease, the fluorescence intensity is increased. Therefore, for example, an increase in fluorescence intensity caused by temperature decrease may be measured while gradually decreasing the temperature of the sample.

Further, in the method of detecting a polymorphism of the present invention, in addition to a polymorphism in the ABCC gene, a polymorphism(s) in at least one selected from the group consisting of the MDR1 gene and the CYP3A5 gene may be detected by using at least one probe selected from the group consisting of a probe for detecting a polymorphism in the MDR1 gene and a probe for detecting a polymorphism in the CYP3A5 gene.

Furthermore, by using in combination a probe for detecting a polymorphism in the ABCC2 gene, a probe for detecting a polymorphism in the MDR1 gene, and a probe for detecting a polymorphism in the CYP3A5 gene, not only may polymorphisms in these three genes be detected easily in one system, but also the tolerance to a drug and the efficacy of a drug may be estimated more correctly.

The method in which plural gene polymorphisms may be detected in one system is not particularly limited. For example, the method may be a method in which individual probes capable of detecting these polymorphisms are preliminarily mixed and the resulting mixture is added to a sample, or a method in which individual probes capable of detecting these polymorphisms are continuously added to a sample containing a single-stranded nucleic acid(s).

The term "system" means an independent reaction system formed with a sample containing a hybrid in which a fluorescently labeled oligonucleotide and a single-stranded nucleic acid are hybridized.

The MDR1 gene in the present invention is already known, and a part of the base sequence thereof corresponds to a sequence of NCBI dbSNP Accession No. rs1045642 (1-511). The base sequence of SEQ ID NO:2 shows a part of the base sequence coding for the MDRI gene.

The CYP3A5 gene in the present invention is already known, and a part of the base sequence thereof is a sequence of NCBI dbSNP Accession No. rs776746 (1-801). The base sequence of SEQ ID NO:3 shows a part of the base sequence coding for the CYP3A5 gene.

Examples of the probe for detecting a polymorphism in the MDR1 gene may include a probe capable of detecting a polymorphism in the exon 26 of the MDR1 gene, and may also include a probe capable of detecting a polymorphism of the 3435th base in the MDR1 gene, but are not limited as long as the probe is a probe capable of detecting a polymorphism in the MDR1 gene.

Examples of such probes for detecting a polymorphism in the MDR1 gene include, for example, probes as described in the probes described in JP-A No. 2005-287335, and also include, for example, a probe consisting of the base sequence indicated in SEQ ID NO:19.

Examples of the probe for detecting a polymorphism in the CYP3A5 gene may include a probe capable of detecting a polymorphism in the intron 3 of the CYP3A5 gene, and may also include a probe capable of detecting a polymorphism of the 6986th base in the CYP3A5 gene, but are not limited as long as the probe is a probe capable of detecting a polymorphism in the CYP3A5 gene. For example, a probe consisting of the base sequence indicated in SEQ ID NO:20 and so on are included.

<Method of Evaluating Drug Efficacy or Tolerance>

The method of evaluating a drug efficacy or tolerance of the present invention includes detecting a polymorphism in the ABCC2 gene by the above-described polymorphism detection method, and evaluating the tolerance to a drug or the efficacy of a drug based on the results of the detection.

In the above-described polymorphism detection method, a polymorphism in the ABCC2 gene may be detected with a high sensitivity and easily by using the probe in the present invention, and therefore, based on this polymorphism in the ABCC2 gene, evaluation of a drug may be carried out with a high sensitivity and easily.

In addition, evaluation of the tolerance to a drug and the efficacy of a drug may be carried out based on whether a polymorphism(s) exists or not and/or based on the abundance ratio of a mutant sequence(s) and/or a normal sequence(s). The method of evaluating the efficacy of a drug of the present invention is useful in, for example, deciding whether the therapeutic strategy of a disease should be shifted so as to increase the dosage of the drug or use another therapeutic agent instead of the drug, based on whether a mutation(s) exists or not and/or based on the abundance ratio of a mutant sequence(s).

Specific examples of a drug to be subjected to the judgment include immunosuppressants, molecularly targeted therapeutic agents, and antidepressants, and especially immunosuppressants and molecularly targeted therapeutic agents.

<Reagent Kit>

The reagent kit for detecting a polymorphism in the ABCC2 gene of the present invention contains the above-described probe.

This reagent kit may contain at least one probe capable of detecting easily and with a high sensitivity a polymorphism of the 207th base of the sequence indicated in SEQ ID NO:1 among polymorphisms in the ABCC2 gene, and this tends, for example, to make it possible to detect a polymorphism in the ABCC2 gene more easily.

In addition, the reagent kit in the present invention may further contain the above-described primer for amplifying a sequence having an ABCC2 gene polymorphism to be detected. This may enable the reagent kit in the present invention to detect a polymorphism in the ABCC2 gene with good accuracy.

In addition to the probe for detecting a polymorphism in the ABCC2 gene, the reagent kit in the present invention may also further contain at least one probe selected from the group consisting of a probe for detecting a polymorphism in the MDR1 gene and a probe for detecting a polymorphism in the CYP3A5 gene as described above.

With regard to a probe(s) and primer(s) that may be contained in the reagent kit, the above descriptions may be applied as they are.

In a case in which two or more types of oligonucleotide are contained as the probes, the oligonucleotides may be contained in a mixed state, or may be contained in the state of being separate from each other.

The two or more types of fluorescent-labeled oligonucleotide may be respectively labeled with fluorescent dyes having different emission wavelengths from each other.

By using the probes labeled with respectively different fluorescent dyes, detection of the signal from each fluorescent-labeled oligonucleotide can simultaneously be carried out even in a single reaction system.

In addition, the reagent kit according to the present invention may further include primers for amplifying a base sequence having a region to which the above-described probe can hybridize. With regard to the probe and the primers that may be included in the reagent kit, the above descriptions thereof may be applied as they are.

Besides the probe and the primers, the reagent kit according to the present invention may further include reagents required for carrying out the nucleic acid amplification in the detection method according to the present invention. The probe, the primers and other reagents may be separately contained, or some of them may be contained in the state of a mixture.

The term "separately contained" may refer to a state in which individual reagents are separated from each other such that the non-contact state therebetween is maintained, and does not necessarily require that the individual reagents be contained in separate containers that can be independently handled.

When the reagent kit includes a primer set for amplifying a base sequence including a base at the gene mutation site (a region to which the probe can hybridize), detection of the gene mutation with higher sensitivity, for example, can be achieved.

The reagent kit according to the present invention may further include an instruction manual that describes instructions for the formation of a differential melting curve for a sample containing a nucleic acid to be detected using the ABCC2 probe, and for the detection of a gene mutation in a gene-encoding base sequence through Tm value analysis based on the differential melting curve, or instructions that describes various reagents that are contained, or may additionally be contained, in the reagent kit.

EXAMPLES

The present invention will now be described in detail by way of examples. However, the present invention is not limited to these examples in any way.

Example 1

PCR and Tm analysis were carried out using a fully-automated SNP analyzer (trade name: I-DENSY (trademark), manufactured by ARKRAY, Inc.) and the reagent for examination of the formulation as shown in Table 4 below. As a polymerase, a Taq polymerase was used.

TABLE 4

Reagent for Examination

Reaction Solution Formulation
(Final Concentration)
Reaction Solution Volume: 50 μl

| | |
|---|---|
| 1 × PCR buffer | |
| dNTP | 0.2 mM |
| MgCl2 | 1.5 mM |
| Taq Polymerase | 1.88 U |
| 100 μM MDR1 F112-131 | 1 μM |
| 100 μM MDR1 R3 | 0.5 μM |
| 100 μM CYP3A5*3 F4 | 0.25 μM |
| 100 μM CYP3A5*3R4 | 0.5 μM |
| 100 μM ABCC2-C-24T-F1 | 0.5 μM |
| 100 μM ABCC2-C-24T-R1 | 1 μM |
| 100 μM 3PB-MDR1-T-R1-19 | 0.4 μM |
| 100 μM 3FL-CYP3A5*3-mt-F21 | 0.2 μM |
| 100 μM 3T-ABCC2-C-24T-mt-F2 | 0.2 μM |

Details of the probes and primers used in Table 4 above are respectively shown in Table 5 and Table 6 below. The parentheses at the 3' end of the probe indicate the type of the fluorescent dye.

TABLE 5

| Probe | name | sequence(5'→3') | (mer) | SEQ ID NO |
|---|---|---|---|---|
| for MDR1 gene polymorphism | 3PB-MDR1-T-R1-19 | ctgccctcacAatctcttc-(Pacific Blue) | 19 | 19 |
| for CYP3A5 gene polymorphism | 3FL-CYP3A5*3-mt-F1-21 | ttgtctttcaGtatctcttcc-(BODIPY FL) | 21 | 20 |
| for ABCC2 gene polymorphism | 3T-ABCC2-C-24T-mt-F2 | tctggaacAaagactcttc-(TAMRA) | 19 | 12 |

TABLE 6

| Primer | name | sequence(5'→3') | (mer) | SEQ ID NO |
|---|---|---|---|---|
| for MDR1 gene polymorphism | MDR1 F112-131 | actgcagcattgctgagaac | 20 | 21 |
| for MDR1 gene polymorphism | MDR1 R3 | cagagaggctgccacatgctc | 21 | 22 |
| for CYP3A5 gene polymorphism | CYP3A5*3 F4 | cgtatgtaccacccagcttaacg | 23 | 23 |
| for CYP3A5 gene polymorphism | CYP3A5*3 R4 | cacaggagccacccaagg | 18 | 24 |
| for ABCC2 gene polymorphism | ABCC2-C-24T-F1 | cttctccagcatgattcctggac | 23 | 17 |
| for ABCC2 gene polymorphism | ABCC2-C-24T-R1 | atcagaatggtagataattcctgttccact | 30 | 18 |

The PCR was carried out by performing a reaction at 95° C. for 60 seconds, and then repeating 50 times a cycle of 95° C. for 1 second and 61° C. for 30 seconds.

The Tm analysis was carried out after the PCR by performing a reaction at 95° C. for 1 second and at 40° C. for 60 seconds, and then measuring the change in the fluorescence intensity over time while raising the temperature from 40° C. to 75° C. at a temperature increasing rate of 1° C. per 3 seconds.

With regard to the fluorescent dye PACIFIC BLUE, the excitation wavelength was in a range from 365 nm to 415 nm, and the detection wavelength was in a range from 445 nm to 480 nm. With regard to the fluorescent dye BODIPY FL, the excitation wavelength was in a range from 420 nm to 485 mu, and the detection wavelength was in a range from 520 nm to 555 nm. With regard to the fluorescent dye TAMRA, the excitation wavelength was in a range from 520 nm to 555 nm, and the detection wavelength was in a range from 585 nm to 700 nm. Based on these wavelengths, the change in the fluorescence intensity derived from each fluorescently labeled probe was measured.

As a template, whole blood and purified genome (manufactured by Roche) were used.

The whole blood was prepared as follows.

To 80 μl of Diluent 1, 10 μl of whole blood was added, and the resultant was mixed well. Thereafter, 10 μl of the mixture was added to 80 μl of Diluent 2. By heating 17 μl of the resulting mixture at 95° C. for 10 minutes, 4 μl of pretreated whole blood was obtained. This was used as a template for 1 test.

TABLE 7

Diluent 1

| Tris-HCl (pH8.0) | 10 mM |
|---|---|
| EDTA (pH8.0) | 0.1 mM |
| SDS | 0.30% |

TABLE 8

Diluent 2

| Tris-HCl (pH8.0) | 10 mM |
|---|---|
| 500 mM EDTA (pH8.0) | 0.1 mM |

With regard to the purified genome, 4 μl of 30 copies/μl purified genome (manufactured by Roche) was used for 1 test.

FIG. 2, which shows the amount of the change in the fluorescence value of the probe, was created from the Tm analysis. In the figures, the ordinate represents the amount of the change in the fluorescence intensity per unit time (d(Amount of Increase in Fluorescence Intensity/t), and the abscissa represents the temperature (° C.).

Figure 2A:
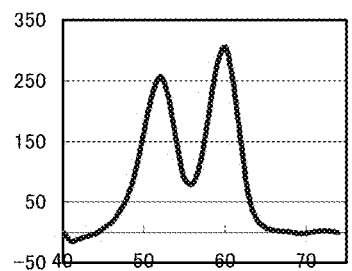
FIG. 2A to FIG. 2F are differential melting curves of samples according to Example 1 of the present invention.

FIG. 2A shows that, in the MDR1 gene in the case where whole blood is used as a template, clear peaks corresponding to each of a peak of a wild type and a peak of a C3435T mutant type may be obtained.

Figure 2D:
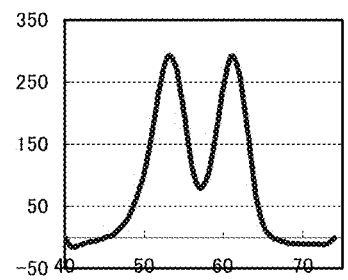

FIG. 2D shows that, in the MDR1 gene in the case where human genome is used as a template, clear peaks corresponding to each of a peak of a wild type and a peak of a C3435T mutant type may be obtained.

Figure 2B:
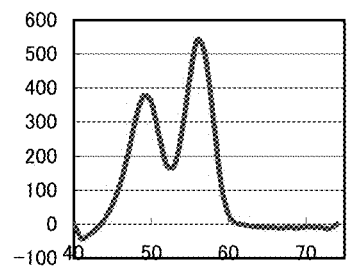

FIG. 2B shows that, in the CYP3A5 gene in the case where whole blood is used as a template, clear peaks corresponding to each of a peak of a wild type (*1) and a peak of a mutant type (*3) may be obtained.

Figure 2E:
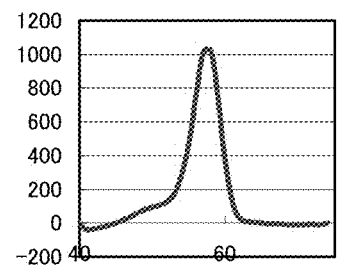

FIG. 2E shows that, in the CYP3A5 gene in the case where human genome is used as a template, a clear peak corresponding to a peak of a mutant type (*3) may be obtained.

Figure 2C:
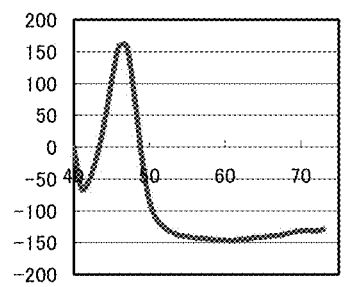

FIG. 2C shows that, in the ABCC2 gene in the case where whole blood is used as a template, a clear peak corresponding to a peak of a wild type may be obtained.

Figure 2F:
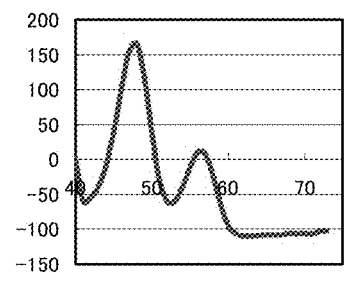

FIG. 2F shows that, in the ABCC2 gene in the case where human genome is used as a template, clear peaks corresponding to each of a peak of a wild type and a peak of a C-24T mutant type may be obtained.

Example 2

Tm analysis was carried out using a fully-automated SNP analyzer (trade name: I-DENSY (trademark), manufactured by ARKRAY, Inc.) and the reaction solution of the formulation as shown in Table 9 below.

TABLE 9

Formulation)

| Reaction Solution Formulation (Final Concentration) Reaction Solution Volume: 50 μl | |
|---|---|
| 1 × PCR buffer | |
| dNTP | 0.2 mM |
| MgCl2 | 1.5 mM |
| 5 μM Probe | 0.4 μM |
| 5 μM Complementary Strand | 0.4 μM |

The Tm analysis was carried out after the PCR by performing a reaction at 95° C. for 1 second and at 40° C. for 60 seconds, and then measuring the change in the fluorescence intensity over time while raising the temperature from 40° C. to 75° C. at a temperature increasing rate of 1° C. per 3 seconds. Since TAMRA was used as a fluorescent dye, the excitation wavelength was in a range from 520 nm to 555 nm, and the detection wavelength was in a range from 585 nm to 700 nm. Based on these wavelengths, the change in the fluorescence intensity derived from each fluorescently labeled probe was measured.

As a probe for detecting a polymorphism, a fluorescently labeled oligonucleotide having a sequence including the 207th to the 217th bases of the sequence indicated in SEQ ID NO:1 and having a length of 19 bases, the base corresponding to the 217th base being labeled with a fluorescent dye (TAMRA) (tctggaacAaagactcttc, SEQ ID NO:12), was used.

As a wild-type template, a single-stranded nucleic acid ABCC2-C—24T-WT (atattaatagaagagtcttTgttccagacgcagtccagga, SEQ ID NO:25) was used; as a mutant-type template, a single-stranded nucleic acid ABCC2-C—24T-mt (atattaatagaagagtcttCgttccagacgcagtccagga, SEQ ID NO:26) was used; and as a mixed-type template, a 1:1 mixture of a single-stranded nucleic acid ABCC2-C—24T-WT and a single-stranded nucleic acid ABCC2-C—24T-mt was used.

Figure 3A:
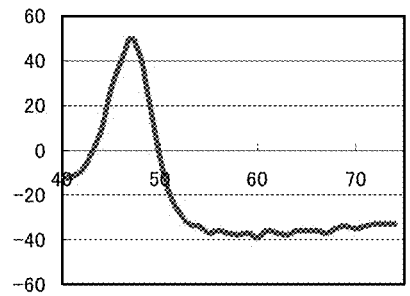
FIG. 3A to FIG. 3C are differential melting curves of samples according to Example 2 of the present invention.
Figure 3B:
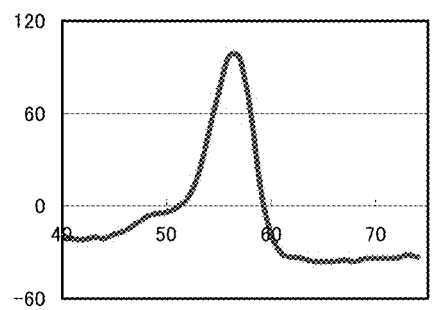
Figure 3C:
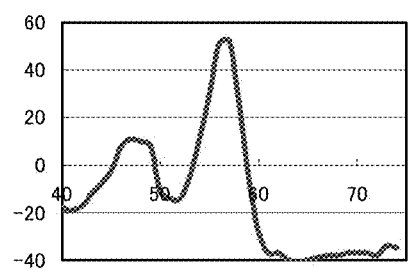

FIG. 3, which shows the amount of the change in the fluorescence value of the probe, was created from the Tm analysis. FIG. 3A shows the result in the case of a wild type; FIG. 3B shows the result in the case of a mutant type; and FIG. 3C shows the result in the case of a mixed type. In the figures, the ordinate represents the amount of the change in the fluorescence intensity per unit time (d(Amount of Increase in Fluorescence Intensity/t), and the abscissa represents the temperature (° C.).

As a result, it was proved that peaks that may be identified as a wild type or a mutant type were obtained in all the cases shown in FIG. 3A to FIG. 3C.

Comparative Example 1

Tm analysis was carried out in the same manner as in Example 2, except that, as a probe for detecting a polymorphism, 3T-ABCC2-C—24T-mt-F1 ((TAMRA)-ctggaacAaagactcttctatt-(phosphorylated)) shown as the base sequence indicated in SEQ ID NO:27 was used instead of the 3T-ABCC2-C—24T-mt-F2 (tctggaacAaagactcttc-(TAMRA)) shown as the base sequence indicated in SEQ ID NO:12.

Figure 4A:
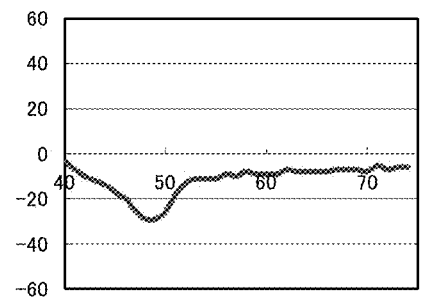
FIG. 4A to FIG. 4C are differential melting curves of samples according to Comparative Example 1 of the present invention.
Figure 4B:
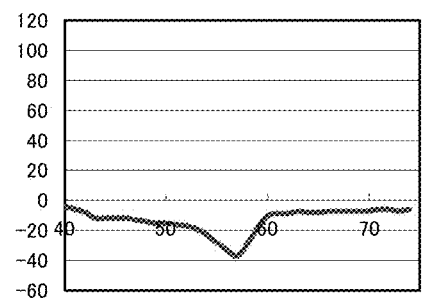
Figure 4C:
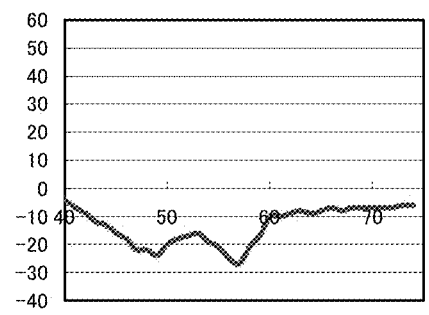

As a result, FIG. 4, which shows the amount of the change in the fluorescence value of the probe, was created. FIG. 4A shows the result in the case of a wild type; FIG. 4B shows the result in the case of a mutant type; and FIG. 4C shows the result in the case of a mixed type. In the figures, the ordinate represents the amount of the change in the fluorescence intensity per unit time (d(Amount of Increase in Fluorescence Intensity/t), and the abscissa represents the temperature (° C.).

In the Tm analysis, the fluorescence value is increased together with the dissociation of the probe associated with the temperature increase, and thereby a convex peak appears, allowing right judgment. However, in the cases where 3T-ABCC2-C—24T-mt-F1 was used as a probe, it was proved that the shape of the peaks was concave as shown in FIG. 4A to FIG. 4C and therefore right judgment was not possible.

Thus, it was proved that the present invention may make it possible to detect a polymorphism in the ABCC2 gene with a high sensitivity and easily.

What is claimed is:

1. A probe consisting of a fluorescently labeled oligonucleotide consisting of a sequence of SEQ ID NO: 12.

2. The probe of claim 1, wherein the fluorescently labeled oligonucleotide is labeled at its 3' end.

3. The probe of claim 1, wherein the fluorescently labeled oligonucleotide emits fluorescence when not hybridized to its target sequence, and the fluorescence intensity of the fluorescently labeled oligonucleotide when hybridized to its target sequence is smaller than the fluorescence intensity when not hybridized to its target sequence.

4. The probe of claim 1, being a probe for melting curve analysis.

5. A method of detecting polymorphism in the ABCC2 gene, the method comprising:

(I) contacting the probe of claim 1 with a single-stranded nucleic acid in a sample and hybridizing the fluorescently labeled oligonucleotide and the single-stranded nucleic acid to obtain a hybrid;

(II) measuring a change of a fluorescent signal based on dissociation of the hybrid by changing the temperature of the sample comprising the hybrid in order to dissociate the hybrid;

(III) determining a value Tm which is a temperature at which the hybrid dissociates based on the fluorescent signal variation; and (IV) determining whether or not polymorphism of the ABCC2 gene is present, or determining the abundance ratio of a nucleic acid having polymorphism, based on the Tm value.

6. The method of claim 5, further comprising amplifying the nucleic acid before (I) or at the same time as (II).

7. The method of claim 5, further comprising detecting an additional polymorphism in at least one selected from the group consisting of the MDR1 gene and the CYP3A5 gene, using at least one probe selected from the group consisting of a probe for detecting polymorphism in the MDR1 gene and a probe for detecting polymorphism in the CYP3A5 gene.

8. A reagent kit for detecting a polymorphism in the ABCC2 gene, comprising the probe of claim 1.

9. The reagent kit of claim 8, further comprising a primer for amplifying a region including a sequence that the P1 fluorescently labeled oligonucleotide hybridizes.

10. The reagent kit of claim 8, further comprising at least one probe selected from the group consisting of a probe for detecting polymorphism in the MDR1 gene and a probe for detecting polymorphism in the CYP3A5 gene.

* * * * *

```
                        SEQUENCE LISTING

<160> NUMBER OF SEQ ID NOS: 27

<210> SEQ ID NO 1
<211> LENGTH: 611
<212> TYPE: DNA
<213> ORGANISM: Homo sapiens
<220> FEATURE:
<221> NAME/KEY: variation
<222> LOCATION: (207)..(207)
<223> OTHER INFORMATION: n is a, g, c or t.
<220> FEATURE:
<221> NAME/KEY: misc_feature
<222> LOCATION: (207)..(207)
<223> OTHER INFORMATION: n is a, c, g, or t

<400> SEQUENCE: 1
ttatgaatta tgctttctaa aaagcctgag ctttagacca attgcacatc taacatttct      60
ggttcttgtt ggtgaccacc ctaagttaac taactaccac ttgttctgag tctgagaaga     120
gtcaatatga agataaatgt aatttctcac ccaaaaagta gagttgcaga acttctccag     180
catgattcct ggactgcgtc tggaacnaag actcttctat taatatgatt gtgttgtttc     240
ttctttactt gtttcatcaa agaaagtgga acaggaatta tctaccattc tgatgttctc     300
cgtaaaggat gacctttcat cccaaccatt taatcgttaa ccttgcctag atgcatgtta     360
cattgaaaca gtggatggac atgtgactaa aaagccctag ggacagggag actcaccagt     420
tcccaaagta caagaggcct ctgtaggagt ggccatacat aaaaggaacc actgaaagat     480
gtcaacagag ctggccaaca aatcaagagt gcacagtctt tcattttcct aaggacatat     540
gacccacaaa gggcagcatc agtagagggg caggcacccc taaatgtgca gtttcgcttc     600
tgctgcaaga t                                                         611
```

<210> SEQ ID NO 2
<211> LENGTH: 506
<212> TYPE: DNA
<213> ORGANISM: Homo sapiens
<220> FEATURE:
<221> NAME/KEY: variation
<222> LOCATION: (256)..(256)
<223> OTHER INFORMATION: n is a, g, c or t.
<220> FEATURE:
<221> NAME/KEY: misc_feature
<222> LOCATION: (256)..(256)
<223> OTHER INFORMATION: n is a, c, g, or t

<400> SEQUENCE: 2

```
ctcacagtaa cttggcagtt tcagtgtaag aaataatgat gttaattgtg ctacattcaa    60
agtgtgctgg tcctgaagtt gatctgtgaa ctcttgtttt cagctgcttg atggcaaaga   120
aataaagcga ctgaatgttc agtggctccg agcacacctg gcatcgtgt cccaggagcc    180
catcctgttt gactgcagca ttgctgagaa cattgcctat ggagacaaca gccgggtggt   240
gtcacaggaa gagatngtga gggcagcaaa ggaggccaac atacatgcct tcatcgagtc   300
actgcctaat gtaagtctct cttcaaataa acagcctggg agcatgtggc agcctctctg   360
gcctatagtt tgatttataa ggggctggtt tcccagaagt gaagagaaat tagcaaccaa   420
atcacaccct tacctgtata caagcatctg gccacacttc ctgtttgggt tagttgttac   480
ctttacctga tcacctgacc ctcctt                                        506
```

<210> SEQ ID NO 3
<211> LENGTH: 801
<212> TYPE: DNA
<213> ORGANISM: Homo sapiens
<220> FEATURE:
<221> NAME/KEY: variation
<222> LOCATION: (401)..(401)
<223> OTHER INFORMATION: r is g or a.

<400> SEQUENCE: 3

```
tttgttcact agaagcaagt gggagaaagc tttgcctctt tgtacttctt catcttctcc    60
cctcaagtcc tcagaatcca cagcgctgac tgtggagtgc tgtggagctg catggcccca   120
tacaggcaac atgacttagt agacagatga cacagctcta gatgtccatg gccccacac    180
caactgccct tgcagcattt agtccttgtg agcacttgat gatttacctg ccttcaattt   240
ttcactgacc taatattctt tttgataatg aagtatttta aacatataaa acattatgga   300
gagtggcata ggagataccc acgtatgtac cacccagctt aacgaatgct ctactgtcat   360
ttctaaccat aatctctttta aagagctctt ttgtctttca rtatctcttc cctgtttgga   420
ccacattacc cttcatcata tgaagccttg ggtggctcct gtgtgagact cttgctgtgt   480
gtcaccct aatgaactag aacctaaggt tgctgtgtgt cgtacaacta ggggtatgga   540
ttacataaca taatgatcaa agtctggctt cctgggtgtg gctccagctg cagaatcggg   600
ctagtgaagt ttaatcagct ccgttgtccc cacacagaac gtatgaaggt caactccctg   660
tgctggccat cacagatccc gacgtgatca gaacagtgct agtgaaagaa tgttattctg   720
tcttcacaaa tcgaagggta agcatccatt ttttgaaatt taaataatga ttgatccact   780
gattaaattt ttattttgaa a                                             801
```

<210> SEQ ID NO 4
<211> LENGTH: 19
<212> TYPE: DNA
<213> ORGANISM: artificial
<220> FEATURE:

```
<223> OTHER INFORMATION: probe 1

<400> SEQUENCE: 4
tctggaacga agactcttc                                                  19

<210> SEQ ID NO 5
<211> LENGTH: 37
<212> TYPE: DNA
<213> ORGANISM: artificial
<220> FEATURE:
<223> OTHER INFORMATION: probe 2

<400> SEQUENCE: 5
catgattcct ggactgcgtc tggaacaaag actcttc                              37

<210> SEQ ID NO 6
<211> LENGTH: 57
<212> TYPE: DNA
<213> ORGANISM: artificial
<220> FEATURE:
<223> OTHER INFORMATION: probe 3

<400> SEQUENCE: 6
catgattcct ggactgcgtc tggaacaaag actcttctat taatatgatt gtgttgt        57

<210> SEQ ID NO 7
<211> LENGTH: 19
<212> TYPE: DNA
<213> ORGANISM: artificial
<220> FEATURE:
<223> OTHER INFORMATION: probe 4

<400> SEQUENCE: 7
tctgcaacga agactcttc                                                  19

<210> SEQ ID NO 8
<211> LENGTH: 37
<212> TYPE: DNA
<213> ORGANISM: Artificial
<220> FEATURE:
<223> OTHER INFORMATION: probe 5

<400> SEQUENCE: 8
aatgatacct ggactgcgtc tggaacaaag actcttc                              37

<210> SEQ ID NO 9
<211> LENGTH: 57
<212> TYPE: DNA
<213> ORGANISM: Artificial
<220> FEATURE:
<223> OTHER INFORMATION: probe 6

<400> SEQUENCE: 9
catgattcct ggactgcgtc tggaacaaag actcttctag gaatatgatt gtgttgt        57

<210> SEQ ID NO 10
<211> LENGTH: 12
<212> TYPE: DNA
<213> ORGANISM: Artificial
<220> FEATURE:
<223> OTHER INFORMATION: probe 7

<400> SEQUENCE: 10
ctaagactct tc                                                         12

<210> SEQ ID NO 11
```

```
<211> LENGTH: 12
<212> TYPE: DNA
<213> ORGANISM: Artificial
<220> FEATURE:
<223> OTHER INFORMATION: probe 8

<400> SEQUENCE: 11
ccaagactct tc                                                         12

<210> SEQ ID NO 12
<211> LENGTH: 19
<212> TYPE: DNA
<213> ORGANISM: Artificial
<220> FEATURE:
<223> OTHER INFORMATION: probe 9

<400> SEQUENCE: 12
tctggaacaa agactcttc                                                  19

<210> SEQ ID NO 13
<211> LENGTH: 19
<212> TYPE: DNA
<213> ORGANISM: Artificial
<220> FEATURE:
<223> OTHER INFORMATION: probe 10

<400> SEQUENCE: 13
tctagaacga agactcttc                                                  19

<210> SEQ ID NO 14
<211> LENGTH: 27
<212> TYPE: DNA
<213> ORGANISM: Artificial
<220> FEATURE:
<223> OTHER INFORMATION: probe 11

<400> SEQUENCE: 14
ggactgcgtc tggaacaaag actcttc                                         27

<210> SEQ ID NO 15
<211> LENGTH: 32
<212> TYPE: DNA
<213> ORGANISM: Artificial
<220> FEATURE:
<223> OTHER INFORMATION: probe 12

<400> SEQUENCE: 15
ttcctgaacc gcgtctggaa caaagactct tc                                   32

<210> SEQ ID NO 16
<211> LENGTH: 32
<212> TYPE: DNA
<213> ORGANISM: Artificial
<220> FEATURE:
<223> OTHER INFORMATION: probe 13

<400> SEQUENCE: 16
ttcctgaacc acgtctggaa cgaagactct tc                                   32

<210> SEQ ID NO 17
<211> LENGTH: 23
<212> TYPE: DNA
<213> ORGANISM: Artificial
<220> FEATURE:
<223> OTHER INFORMATION: primer 1

<400> SEQUENCE: 17
```

```
cttctccagc atgattcctg gac                                              23

<210> SEQ ID NO 18
<211> LENGTH: 30
<212> TYPE: DNA
<213> ORGANISM: Artificial
<220> FEATURE:
<223> OTHER INFORMATION: primer 2

<400> SEQUENCE: 18
atcagaatgg tagataattc ctgttccact                                       30

<210> SEQ ID NO 19
<211> LENGTH: 19
<212> TYPE: DNA
<213> ORGANISM: Artificial
<220> FEATURE:
<223> OTHER INFORMATION: probe MDR1-1

<400> SEQUENCE: 19
ctgccctcac aatctcttc                                                   19

<210> SEQ ID NO 20
<211> LENGTH: 21
<212> TYPE: DNA
<213> ORGANISM: Artificial
<220> FEATURE:
<223> OTHER INFORMATION: probe CUP3A5

<400> SEQUENCE: 20
ttgtctttca gtatctcttc c                                                21

<210> SEQ ID NO 21
<211> LENGTH: 20
<212> TYPE: DNA
<213> ORGANISM: Artificial
<220> FEATURE:
<223> OTHER INFORMATION: primer MDR1-F1

<400> SEQUENCE: 21
actgcagcat tgctgagaac                                                  20

<210> SEQ ID NO 22
<211> LENGTH: 21
<212> TYPE: DNA
<213> ORGANISM: Artificial
<220> FEATURE:
<223> OTHER INFORMATION: primer MDR1-R1

<400> SEQUENCE: 22
cagagaggct gccacatgct c                                                21

<210> SEQ ID NO 23
<211> LENGTH: 23
<212> TYPE: DNA
<213> ORGANISM: Artificial
<220> FEATURE:
<223> OTHER INFORMATION: primer CYP3A5-F1

<400> SEQUENCE: 23
cgtatgtacc acccagctta acg                                              23

<210> SEQ ID NO 24
<211> LENGTH: 18
<212> TYPE: DNA
<213> ORGANISM: Artificial
<220> FEATURE:
```

```
<223> OTHER INFORMATION: primer CYP3A5-R1

<400> SEQUENCE: 24
cacaggagcc acccaagg                                                    18

<210> SEQ ID NO 25
<211> LENGTH: 40
<212> TYPE: DNA
<213> ORGANISM: Artificial
<220> FEATURE:
<223> OTHER INFORMATION: template 1

<400> SEQUENCE: 25
atattaatag aagagtctttt gttccagacg cagtccagga                           40

<210> SEQ ID NO 26
<211> LENGTH: 40
<212> TYPE: DNA
<213> ORGANISM: Artificial
<220> FEATURE:
<223> OTHER INFORMATION: template 2

<400> SEQUENCE: 26
atattaatag aagagtcttc gttccagacg cagtccagga                            40

<210> SEQ ID NO 27
<211> LENGTH: 22
<212> TYPE: DNA
<213> ORGANISM: Artificial
<220> FEATURE:
<223> OTHER INFORMATION: probe X-1

<400> SEQUENCE: 27
ctggaacaaa gactcttcta tt                                               22
```